(12) United States Patent
Yasugi et al.

(10) Patent No.: US 10,667,675 B2
(45) Date of Patent: Jun. 2, 2020

(54) IMAGING DEVICE AND IMAGE PROCESSING METHOD

(71) Applicant: Panasonic Corporation, Osaka (JP)

(72) Inventors: Shunsuke Yasugi, Osaka (JP); Taro Imagawa, Osaka (JP); Shinsaku Hiura, Hyogo (JP)

(73) Assignee: Panasonic Corporation, Osaka (JP)

( * ) Notice: Subject to any disclaimer, the term of this patent is extended or adjusted under 35 U.S.C. 154(b) by 558 days.

(21) Appl. No.: 15/657,184

(22) Filed: Jul. 23, 2017

(65) Prior Publication Data

US 2017/0319052 A1 Nov. 9, 2017

Related U.S. Application Data

(63) Continuation of application No. PCT/JP2016/003936, filed on Aug. 30, 2016.

(30) Foreign Application Priority Data

Feb. 18, 2016 (JP) .................................. 2016-028450

(51) Int. Cl.
 *A61B 1/00* (2006.01)
 *A61B 1/04* (2006.01)
 (Continued)

(52) U.S. Cl.
 CPC ............ *A61B 1/043* (2013.01); *A61B 1/00* (2013.01); *A61B 1/00009* (2013.01); *A61B 1/00186* (2013.01); *A61B 1/06* (2013.01); *A61B 1/0638* (2013.01); *A61B 5/0075* (2013.01); *A61B 5/0084* (2013.01); *G01N 21/6456* (2013.01); *G01N 2021/6419* (2013.01); *G01N 2021/6421* (2013.01)

(58) Field of Classification Search
 CPC .............. A61B 1/043; A61B 1/06; A61B 1/00
 See application file for complete search history.

(56) References Cited

U.S. PATENT DOCUMENTS

| | | | |
|---|---|---|---|
| 2006/0247537 A1 | 11/2006 | Matsumoto | |
| 2010/0067002 A1 | 3/2010 | Ishii | |
| 2013/0317371 A1 | 11/2013 | Takei | |

FOREIGN PATENT DOCUMENTS

| | | |
|---|---|---|
| JP | 2006-296635 | 11/2006 |
| JP | 2010-068925 | 4/2010 |
| WO | 2013/084566 | 6/2013 |

OTHER PUBLICATIONS

International Search Report of PCT application No. PCT/JP2016/003936 dated Nov. 29, 2016.

*Primary Examiner* — Joseph M Santos Rodriguez
(74) *Attorney, Agent, or Firm* — Wenderoth, Lind & Ponack, L.L.P.

(57) ABSTRACT

A lighting unit has a plurality of light sources that emits excitation light having relative spectral distributions different from each other. An imaging unit simultaneously captures an image of fluorescent light emitted from the subject by the excitation light and an image of reflected light obtained by reflecting the excitation light by the subject, to generate a captured image. The arithmetic unit calculates a relative spectral distribution of the fluorescent light emitted from the subject by using the information about the relative spectral distribution of the reflected light for each of the plurality of light sources stored in the memory and the captured image for each of the plurality of light sources generated by the imaging unit.

13 Claims, 4 Drawing Sheets

(51) Int. Cl.
*G01N 21/64* (2006.01)
*A61B 5/00* (2006.01)
*A61B 1/06* (2006.01)

IMAGING DEVICE AND IMAGE PROCESSING METHOD

BACKGROUND

1. Technical Field

The present disclosure relates to an imaging device that irradiates a subject with excitation light and calculates a relative spectral distribution of fluorescent light emitted from the subject.

2. Description of the Related Art

WO 2013/084566 A discloses an endoscopic device having a light source, an excitation light cut filter, a color filter, an imaging unit, and an image processor. The light source emits excitation light of a first wavelength band and reference light of a second wavelength band to a biological tissue, to which a fluorescent substance has been administered. The excitation light cut filter cuts off the excitation light. The color filter includes a first filter and a second filter. The first filter has relatively high transmittance of a third wavelength band that includes a wavelength band of fluorescent light emitted from the fluorescent substance, and the second filter has relatively high transmittance of the second wavelength band. The imaging unit generates an image in accordance with intensity of return light received when the excitation light and the reference light are simultaneously emitted to the biological tissue, to which the fluorescent substance has been administered. The image processor respectively acquires, from respective color components included in the image, a first image obtained by separating a signal component generated by receiving the fluorescent light and a second image obtained by separating a signal component generated by receiving the reference light.

With this configuration, fluorescent light observation can be performed with an inexpensive and versatile configuration.

SUMMARY

The present disclosure provides an imaging device that calculates a relative spectral distribution of fluorescent light having high resolution with a simple configuration.

The imaging device of the present disclosure includes a lighting unit, an imaging unit, a memory, and an arithmetic unit. The lighting unit has a plurality of light sources that emits excitation light having relative spectral distributions different from each other. The lighting unit causes each of the plurality of light sources to irradiate a subject with excitation light. For each of the plurality of light sources, the imaging unit simultaneously captures an image of fluorescent light emitted from the subject by the excitation light and an image of reflected light obtained by reflecting the excitation light by the subject, to generate a captured image. The memory stores information about a relative spectral distribution of the reflected light for each of the plurality of light sources. The arithmetic unit calculates a relative spectral distribution of the fluorescent light emitted from the subject by using the information about the relative spectral distribution of the reflected light for each of the plurality of light sources stored in the memory and the captured image for each of the plurality of light sources generated by the imaging unit.

Further, an image processing method of the present disclosure includes: irradiating a subject with excitation light from each of a plurality of light sources that emits excitation light having relative spectral distributions different from each other; for each of the plurality of light sources, simultaneously capturing an image of fluorescent light emitted from the subject by the excitation light and an image of reflected light obtained by reflecting the excitation light by the subject, to generate a captured image; and calculating a relative spectral distribution of the fluorescent light emitted from the subject by using information about a relative spectral distribution of the reflected light for each of the plurality of light sources and the generated captured image for each of the plurality of light sources.

According to the present disclosure, there can be provided an imaging device that calculates a relative spectral distribution of fluorescent light having high resolution with a simple configuration.

DETAILED DESCRIPTION

Circumstances Leading to the Present Disclosure

A subject that emits fluorescent light upon irradiation with excitation light emits observation light in which the fluorescent light and reflected light obtained by reflecting the excitation light by the subject are mixed. Accordingly, in an imaging device for capturing an image of fluorescent light, it is necessary that the fluorescent light and the reflected light are separated from the observation light.

Conventionally, an imaging device configured to include a hyperspectral camera as an imaging unit has been known. Due to high wavelength resolution, the hyperspectral camera can separate fluorescent light and reflected light that have wavelengths different from each other, as described below. However, in order to capture an image of the fluorescent light in a two-dimensional manner, the hyperspectral camera is required to scan and capture the image of the fluorescent light. Accordingly, it is difficult to achieve both high spatial resolution and high temporal resolution in the imaging device configured to include the hyperspectral camera. In other words, it is difficult to acquire a relative spectral distribution of the fluorescent light having high resolution in the above-described imaging device. Further, since the hyperspectral camera is generally expensive, the imaging device also becomes expensive.

Further, an imaging device configured to include a color filter as disclosed in WO 2013/084566 A has been conventionally known. The imaging device configured to include the color filter can capture an image of fluorescent light without scanning the fluorescent light. However, it is necessary to change the color filter in order to acquire the fluorescent light and reflected light separately. As a result, the configuration of the imaging device becomes complicated.

In other words, in the conventional imaging device, it is difficult to acquire the relative spectral distribution of the fluorescent light having high resolution with a simple configuration.

Therefore, an imaging device according to the present disclosure includes an imaging unit having high spatial resolution and temporal resolution, such as an RGB camera, and calculates a relative spectral distribution of fluorescent light by calculation. With this configuration, it is possible to realize an imaging device that calculates a relative spectral distribution of fluorescent light having high resolution with a simple configuration.

Hereinafter, exemplary embodiments are described in detail while appropriately referring to the drawings. However, detailed description beyond necessity may be omitted. For example, detailed description of a matter that has been already known well or overlapping description of substantially the same configuration may be omitted. This is to avoid unnecessary redundancy of the following description and to be easily understood by those skilled in the art.

It should be noted that the attached drawings and the following description are provided for those skilled in the art to fully understand the present disclosure, and are not intended to limit the subject matter as described in the appended claims.

First Exemplary Embodiment

A first exemplary embodiment is described with reference to FIGS. 1 and 2.

[1-1. Configuration]

[1-1-1. Fluorescent Light and Spectral Distribution]

Fluorescent light is light emitted from a substance, and reflects a characteristic of the substance. Accordingly, the fluorescent light can be utilized for qualitative and quantitative analysis of the substance. The fluorescent light is generated when the substance is irradiated with light (excitation light) having a wavelength of a specific range capable of generating the fluorescent light. A wavelength of the fluorescent light is basically longer than the wavelength of the excitation light.

A spectral distribution is obtained, for example, by continuously separating light for every wavelength by diffraction grating. In the spectral distribution, a horizontal axis represents a wavelength of the light, and a vertical axis represents intensity of the light at each wavelength. For example, in the spectral distribution of the fluorescent light, qualitative information of the substance that emits the fluorescent light is reflected on its distribution shape, and quantitative information of the substance that emits the fluorescent light is reflected on its overall intensity. Further, the spectral distribution representing the qualitative information is referred to as a relative spectral distribution. In other words, in the present disclosure, even when the spectral distributions have intensity different from each other, the respective spectral distributions are treated as an identical relative spectral distribution as long as the respective spectral distributions have an identical distribution shape. The spectral distribution in the present disclosure may be a continuous distribution for every wavelength, or may be a discrete distribution for every wavelength. Further, the spectral distribution in the present disclosure may be a distribution subjected to integration in a wavelength direction and converted into color information, such as an RGB vector described below.

The fluorescent light has a characteristic in which the relative spectral distribution is not changed by the excitation light having any wavelength, as long as the excitation light has a wavelength capable of generating the fluorescent light. In other words, even when the substance is irradiated with the excitation light having wavelengths different from each other, the relative spectral distributions of the respective fluorescent light emitted from the substance are identical.

The imaging device of the present disclosure utilizes a point that a relative spectral distribution of the fluorescent light is not changed by a relative spectral distribution of the excitation light.

[1-1-2. RGB Vector]

In the present exemplary embodiment, an RGB value of each pixel of a captured image captured by an RGB camera is considered as a three-dimensional vector, and the RGB value is written as an RGB vector. A direction and a length of the RGB vector are described below.

The direction of the RGB vector is information reflecting a ratio of each RGB color, and includes information about a qualitative characteristic of a substance that emits light. In other words, the direction of the RGB vector relates to a relative spectral distribution. For example, an RGB vector with a length normalized to 1 can be used as the direction of the RGB vector. On the other hand, the length of the RGB vector is a value reflecting overall intensity of the RGB, and includes information about a quantitative characteristic of the substance that emits light.

In a case where an image of light having a certain spectral distribution is captured by the RGB camera, each value of an RGB vector of a certain pixel included in a captured image is a value multiplied and further integrated by the spectral distribution of the light and each spectral sensitivity characteristic of R (red), G (green), B (blue) of an imaging element. Accordingly, in a case where the image of the light is captured by the same RGB camera, directions of the RGB vectors are identical as long as relative spectral distributions of the light are identical. In other words, the direction of the RGB vector includes information about the relative spectral distribution of the light. Further, when only intensity of the light is changed while the relative spectral distribution of the light is kept identical, only the length of the RGB vector is changed. In other words, the length of the RGB vector includes information about the intensity of the spectral distribution of the light. Note that, in the present exemplary embodiment, it is considered that the RGB vector is also one of the spectral distributions and that the direction of the RGB vector is also one of the relative spectral distributions. Accordingly, the RGB vector is also written as the spectral distribution, and the direction of the RGB vector is also written as the relative spectral distribution.

Here, an RGB vector of fluorescent light obtained by irradiating a substance that generates certain fluorescent light with excitation light having certain intensity is referred to as vector V1, and an RGB vector of fluorescent light obtained by irradiating the substance with excitation light having double intensity is referred to as vector V2. Then, directions of vector V1 and vector V2 are not different, but a length of vector V2 is twice a length of vector V1.

[1-1-3. Configuration of Imaging Device]

Figure 1:
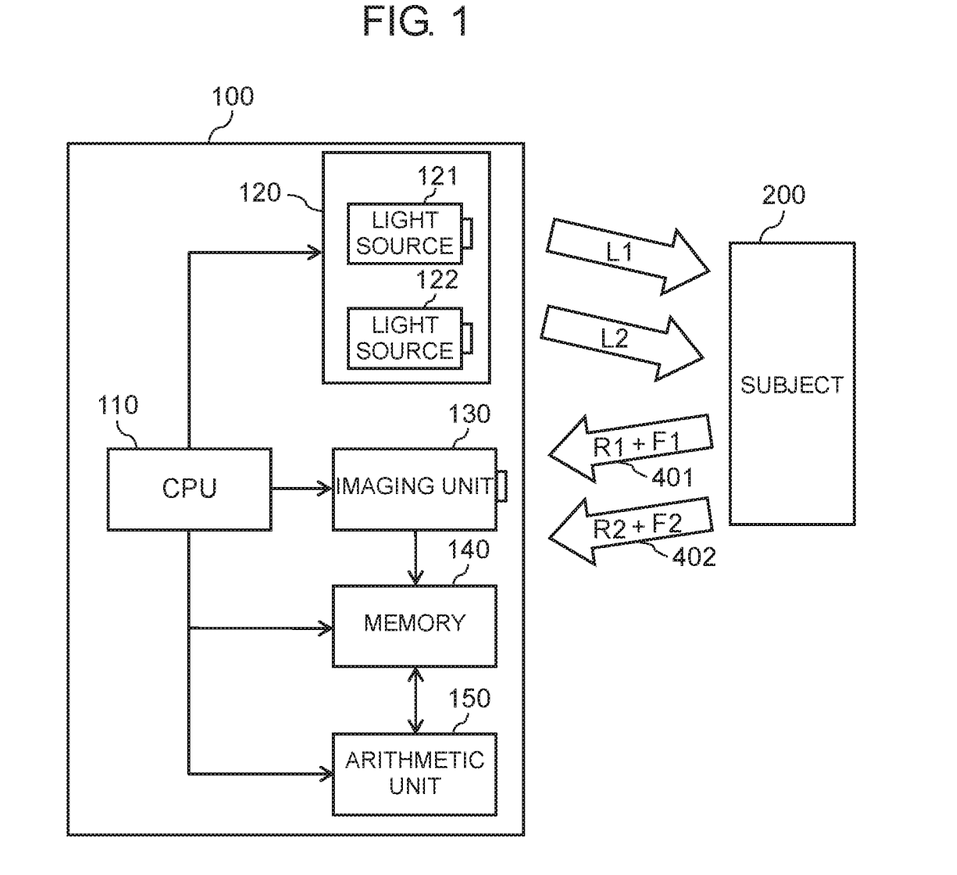
FIG. 1 is a block diagram showing a configuration of an imaging device according to a first exemplary embodiment.

FIG. 1 is a block diagram showing a configuration of imaging device 100 in the first exemplary embodiment.

Imaging device 100 includes CPU (Central Processing Unit) 110, lighting unit 120, imaging unit 130, memory 140, and arithmetic unit 150. Lighting unit 120 has light source 121 and light source 122.

CPU 110 controls operation of the respective units. For example, CPU 110 controls lighting unit 120 to turn on/off light source 121, light source 122. Further, CPU 110 instructs imaging unit 130 to capture an image.

Lighting unit 120 has light source 121, light source 122 that emit excitation light having relative spectral distributions different from each other, and causes each light source to irradiate subject 200 with the excitation light. In the present exemplary embodiment, light source 121 is an LED (Light Emitting Diode), and emits excitation light L1 having a relative spectral distribution of a narrow wavelength band with a wavelength of 430 nm as a center. Further, light source 122 is an LED, and emits excitation light L2 having a relative spectral distribution of a narrow wavelength band with a wavelength of 450 nm as a center. Lighting unit 120 causes light source 121 or light source 122 to emit light according to the control of CPU 110 and to irradiate subject 200 with the excitation light.

By the irradiation of excitation light L1 from light source 121 and the irradiation of excitation light L2 from light source 122, subject 200 emits fluorescent light having an identical relative spectral distribution. Upon irradiation with the excitation light, subject 200 emits observation light in which reflected light obtained by reflecting the excitation light and the fluorescent light emitted by the excitation light are mixed. In FIG. 1, observation light 401 emitted from subject 200 with respect to excitation light L1 is light in which reflected light R1 and fluorescent light F1 are mixed. Further, observation light 402 emitted from subject 200 with respect to excitation light L2 is light in which reflected light R2 and fluorescent light F2 are mixed.

Imaging unit 130 includes a lens and an imaging element. The lens included in imaging unit 130 forms an image of subject 200 by observation light 401 or observation light 402 emitted from subject 200 on the imaging element. The imaging element included in imaging unit 130 has pixels of an RGB Bayer array, and is capable of capturing a color image of three colors. For each light source, imaging unit 130 simultaneously captures an image of the fluorescent light emitted from subject 200 by the excitation light and an image of the reflected light obtained by reflecting the excitation light by subject 200, to generate a captured image. In other words, for each light source, imaging unit 130 captures an image of the observation light in which the excitation light and the fluorescent light are mixed, to generate the captured image. Imaging unit 130 captures the image of subject 200 as a color captured image, and stores the image in memory 140. In the present exemplary embodiment, an RGB camera with high spatial resolution and temporal resolution is used as imaging unit 130. The RGB camera is relatively less expensive than a hyperspectral camera. In the RGB camera, the fluorescent light and the reflected light are included in a same pixel and images thereof are captured in a mixed state.

Memory 140 stores the captured image generated by imaging unit 130. Further, memory 140 is used as a work memory of arithmetic unit 150. Moreover, memory 140 stores information about a relative spectral distribution of the reflected light for each light source. In the first exemplary embodiment, memory 140 stores each spectral information of light source 121 and light source 122 as information about the relative spectral distribution of the reflected light for each light source. Here, each spectral information of light source 121 and light source 122 is information about a relative spectral distribution of the excitation light from each light source. More specifically, the information about the relative spectral distribution of the excitation light from each light source is information about the direction of the RGB vector in a case where an image of the excitation light from each light source is respectively captured by imaging unit 130. In other words, the information about the relative spectral distribution of the excitation light from each light source is an RGB vector of each excitation light. Here, the length of the RGB vector of each excitation light stored in memory 140 is normalized to 1. It should be noted that the length of the RGB vector of each excitation light stored in memory 140 may not be normalized to 1. The RGB vector of each excitation light may have any length, or may have a length that reflects information about the intensity of each excitation light.

Arithmetic unit 150 calculates a relative spectral distribution of the fluorescent light emitted from subject 200 by using information about the relative spectral distribution of the reflected light for each light source stored in memory 140 and the captured image for each light source captured by imaging unit 130. In the first exemplary embodiment, arithmetic unit 150 performs arithmetic processing described below and calculates the relative spectral distribution of the fluorescent light by using spectral information for each light source, that is, each spectral information of light source 121 and light source 122, and the captured image for each light source captured by imaging unit 130. A common relative spectral distribution of the fluorescent light is included in a plurality of spectral distributions of the observation light obtained by respectively irradiating subject 200 with the excitation light having different relative spectral distributions. Arithmetic unit 150 calculates the relative spectral distribution of the fluorescent light by utilizing this point. In the present exemplary embodiment, fluorescent light F1 and fluorescent light F2 have a common relative spectral distribution, that is, an RGB vector having an identical direction.

Further, arithmetic unit 150 also calculates spectral distributions, that is, RGB vectors, of fluorescent light F1 and fluorescent light F2. Moreover, arithmetic unit 150 calculates a spectral distribution of the reflected light, that is, an RGB vector of the reflected light, by using the calculated relative spectral distribution of the fluorescent light, that is, the RGB vector of the fluorescent light having the identical direction. Arithmetic unit 150 calculates a fluorescent light image by using the spectral distribution of the fluorescent light, that is, the RGB vector of the fluorescent light, and calculates a reflected light image by using the spectral distribution of the reflected light, that is, the RGB vector of the reflected light. More specifically, arithmetic unit 150 calculates the fluorescent light image and the reflected light image from the captured image. In other words, arithmetic unit 150 separates the captured image into the fluorescent light image and the reflected light image.

Arithmetic unit 150 may be implemented in such a way that CPU 110 executes a program stored in memory 140.

It should be noted that, in the present exemplary embodiment, only light source 121 and light source 122 are used during the imaging of subject 200, and an image of subject 200 is captured in a darkroom. Further, imaging unit 130 captures an image of subject 200 at a predetermined angle of view, and subject 200 is stationary. In other words, in each captured image of subject 200 captured by imaging unit 130, the image of subject 200 is captured in the same positional relation.

[1-2. Operation]

[1-2-1. Operation of Imaging Device]

Operation of imaging device 100 configured as above is described below.

Figure 2:
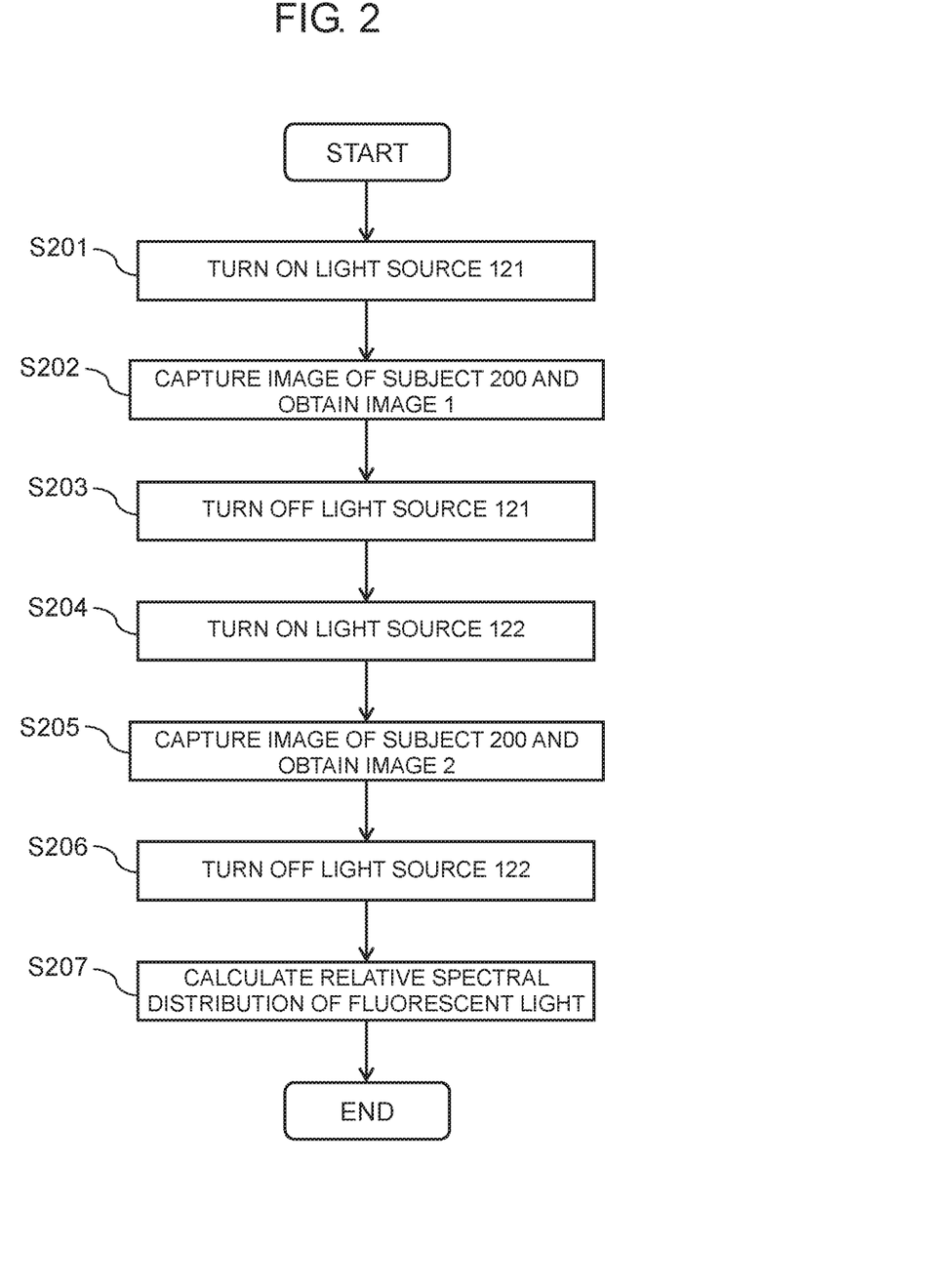
FIG. 2 is a flowchart for describing operation of the imaging device according to the first exemplary embodiment.

FIG. 2 is a flowchart for describing the operation of imaging device 100.

(Step S201) CPU 110 controls lighting unit 120 to turn on light source 121. Lighting unit 120 turns on light source 121, and irradiates subject 200 with excitation light L1. Upon irradiation with excitation light L1, subject 200 emits observation light 401 in which reflected light R1 and fluorescent light F1 are mixed.

(Step S202) CPU 110 causes imaging unit 130 to capture an image of subject 200 in a state where subject 200 is irradiated with excitation light L1. Imaging unit 130 captures an image of observation light 401 emitted from subject 200, to generate image 1. Image 1 is a captured image that simultaneously includes fluorescent light F1 emitted from subject 200 by excitation light L1 and reflected light R1 obtained by reflecting excitation light L1 by subject 200. Imaging unit 130 stores image 1 in memory 140.

(Step S203) When the imaging in step S202 is finished, CPU 110 controls lighting unit 120 to turn off light source 121. Lighting unit 120 turns off light source 121.

(Step S204) CPU 110 controls lighting unit 120 to turn on light source 122. Lighting unit 120 turns on light source 122, and irradiates subject 200 with excitation light L2. Upon irradiation with excitation light L2, subject 200 emits observation light 402 in which reflected light R2 and fluorescent light F2 are mixed.

(Step S205) CPU 110 causes imaging unit 130 to capture an image of subject 200 in a state where subject 200 is irradiated with excitation light L2. Imaging unit 130 captures an image of observation light 402 emitted from subject 200, to generate image 2. Image 2 is a captured image that simultaneously includes fluorescent light F2 emitted from subject 200 by excitation light L2 and reflected light R2 obtained by reflecting excitation light L2 by subject 200. Imaging unit 130 stores image 2 in memory 140.

(Step S206) When the imaging in step S205 is finished, CPU 110 controls lighting unit 120 to turn off light source 122. Lighting unit 120 turns off light source 122.

(Step S207) CPU 110 causes arithmetic unit 150 to calculate the relative spectral distribution of the fluorescent light by using image 1 and image 2 stored in memory 140 and each spectral information of light source 121 and light source 122. Arithmetic unit 150 calculates the relative spectral distribution of the fluorescent light for each pixel of image 1 and image 2. Arithmetic unit 150 calculates the fluorescent light image by using the calculated relative spectral distribution of the fluorescent light. Further, arithmetic unit 150 may calculate the reflected light image by using image 1 and image 2, each spectral information of light source 121 and light source 122, and the calculated relative spectral distribution of the fluorescent light.

[1-2-2. Calculation of Relative Spectral Distribution of Fluorescent Light]

The calculation in step S207 is described in detail.

The calculation is performed by using pixels respectively located at spatially same positions in image 1 and image 2. An imaging element capable of capturing a color image included in imaging unit 130 has a Bayer array structure in which a plurality of color filters are arranged in a checked pattern. Accordingly, only one color value is included in one pixel. Because of this, it is necessary that a color value that is not included in the pixel is created and a plurality of color values is included in one pixel by an interpolation process using color values of peripheral pixels. The method for providing a plurality of color values in one pixel is not limited to the interpolation process, and any process can be used for the method. Other than the imaging element having the Bayer array structure, there is an imaging element in which a plurality of color values are included in one pixel from a state of a device. Thus, imaging unit 130 may include such an imaging element.

Hereinafter, description is given using a pixel of captured subject 200 emitting the fluorescent light as a target. The description is given using a pixel of captured subject 200 in image 1 as pixel p1 and a pixel spatially located at a position identical to a position of pixel p1 in image 2 as pixel p2. Further, each RGB vector is a vector including a spectral sensitivity characteristic of the imaging element. Further, each RGB vector of excitation light L1 and excitation light L2 can be set to any length depending on intensity of each excitation light. Accordingly, the normalized RGB vector of each excitation light is used for the calculation in the present exemplary embodiment.

The RGB vector of pixel p1 is a sum of the RGB vector of reflected light R1 and the RGB vector of fluorescent light F1. Similarly, the RGB vector of pixel p2 is a sum of the RGB vector of reflected light R2 and the RGB vector of fluorescent light F2. Here, light source 121 and light source 122 are LEDs having narrow wavelength bands. Accordingly, it can be considered that directions of the respective RGB vectors of reflected light R1 and reflected light R2 are identical to directions of the respective RGB vectors of excitation light L1 and excitation light L2. Therefore, in image 1, it can be considered that the direction of the RGB vector of reflected light R1 and the direction of the RGB vector of excitation light L1 stored in memory 140 are identical. Similarly, in image 2, it can be considered that the direction of the RGB vector of reflected light R2 and the direction of the RGB vector of excitation light L2 stored in memory 140 are identical.

With this configuration, the RGB vector of pixel p1 can be represented as a linear combination of the RGB vector of excitation light L1 and a vector indicating the direction of the RGB vector of fluorescent light F1. Similarly, the RGB vector of pixel p2 can be represented as a linear combination of the RGB vector of excitation light L2 and a vector indicating the direction of the RGB vector of fluorescent light F2. Since pixel p1 and pixel p2 each include the fluorescent light having the identical relative spectral distribution, the RGB vector of fluorescent light F1 and the RGB vector of fluorescent light F2 can be respectively represented as vectors in the same direction.

Here, the RGB vector of pixel p1 is vector I1=(I1$_R$, I1$_G$, I1$_B$), the RGB vector of excitation light L1 is vector r1=(r1$_R$, r1$_G$, r1$_B$), and the vector indicating the direction of the RGB vector of fluorescent light F1 is vector f=(f$_R$, f$_G$, f$_B$). With this configuration, vector I1 is represented by the following formula:

$$\begin{pmatrix} I1_R \\ I1_G \\ I1_B \end{pmatrix} = a_1 \begin{pmatrix} r1_R \\ r1_G \\ r1_B \end{pmatrix} + b_1 \begin{pmatrix} f_R \\ f_G \\ f_B \end{pmatrix} \qquad \text{(Formula 1)}$$

wherein $a_1$ is a weight of vector r1, and $b_1$ is a weight of vector f.

Further, the RGB vector of pixel p2 is vector I2=(I2$_R$, I2$_G$, I2$_B$), and the RGB vector of excitation light L2 is vector r2=(r2$_R$, r2$_G$, r2$_B$). The vector indicating a direction of the RGB vector of fluorescent light F2 can be represented by vector f which is identical to the vector indicating the direction of the RGB vector of fluorescent light F1. With this configuration, the vector I2 is represented by the following formula:

$$\begin{pmatrix} I2_R \\ I2_G \\ I2_B \end{pmatrix} = a_2 \begin{pmatrix} r2_R \\ r2_G \\ r2_B \end{pmatrix} + b_2 \begin{pmatrix} f_R \\ f_G \\ f_B \end{pmatrix} \quad \text{(Formula 2)}$$

wherein $a_2$ is a weight of vector r2, and $b_2$ is a weight of vector f.

Here, in the respective RGB vectors of fluorescent light F1 and fluorescent light F2, in order to solve instability of a length of vector f and sizes of weights $b_1$, $b_2$, $b_1$ is fixed to 1. This can reduce a number of unknowns by one.

With this configuration, intensity of fluorescent light F1 included in pixel p1 is reflected on the length of vector f. On the other hand, intensity of fluorescent light F2 included in pixel p2 is reflected on weight $b_2$ as a ratio to the intensity of fluorescent light F1 included in pixel p1.

Since six equations with six unknowns, that is, $a_1$, $a_2$, $b_2$, $f_R$, $f_G$, $f_B$, are obtained from (Formula 1), (Formula 2) as described above, it is possible to calculate the respective unknowns.

Further, the respective unknowns may be calculated from seven equations with seven unknowns by adding an equation that normalizes the length of vector f to an arbitrary constant while $b_1$ is remained as an unknown.

Moreover, in pixel p1, the RGB vector of reflected light R1 of pixel p1 can be calculated from a product of $a_1$ and vector r1. Further, the RGB vector of fluorescent light F1 of pixel p1 can be calculated from a product of $b_1$ (=1) and vector f. These RGB vectors respectively correspond to a first term and a second term on a right-hand side of (Formula 1).

Further, in pixel p2, the RGB vector of reflected light R2 of pixel p2 can be calculated from a product of $a_2$ and vector r2. Further, the RGB vector of fluorescent light F2 of pixel p2 can be calculated from a product of b2 and vector f. These RGB vectors respectively correspond to a first term and a second term on a right-hand side of (Formula 2).

Arithmetic unit 150 can calculate a relative spectral distribution of the fluorescent light using image 1 and image 2 by performing the above-described calculation. Further, arithmetic unit 150 can calculate an image reflecting the relative spectral distribution of the fluorescent light by performing the above-described calculation on all target pixels. Further, arithmetic unit 150 can calculate the reflected light image and the fluorescent light image by using the calculated relative spectral distribution of the fluorescent light and the respective spectral information of light source 121 and light source 122. In other words, arithmetic unit 150 can calculate the fluorescent light image by using the calculated relative spectral distribution of the fluorescent light and the information about the relative spectral distribution of the reflected light. Further, arithmetic unit 150 can calculate the reflected light image by using the calculated relative spectral distribution of the fluorescent light and the information about the relative spectral distribution of the reflected light. With this configuration, the reflected light image and the fluorescent light image included in image 1 are separated from image 1, and the reflected light image and the fluorescent light image included in image 2 are separated from image 2. Since the reflected light image and the fluorescent light image respectively separated from image 1, image 2 have the RGB vectors in the respective pixels, the reflected light image and the fluorescent light image are color images.

[1-3. Conclusion]

Imaging device 100 of the first exemplary embodiment includes lighting unit 120, imaging unit 130, memory 140, and arithmetic unit 150. Lighting unit 120 has light source 121, light source 122 that emit excitation light having relative spectral distributions different from each other, and causes each light source to irradiate subject 200 with the excitation light. For each light source, imaging unit 130 simultaneously captures an image of the fluorescent light emitted from subject 200 by the excitation light and an image of the reflected light obtained by reflecting the excitation light by subject 200, to generate a captured image. Memory 140 stores information about the relative spectral distribution of each excitation light from light source 121, light source 122. Arithmetic unit 150 calculates a relative spectral distribution of the fluorescent light emitted from subject 200 by using the information about the relative spectral distribution of the excitation light for each light source stored in memory 140 and image 1, image 2 generated by imaging unit 130.

With this configuration, arithmetic unit 150 can calculate the relative spectral distribution of the fluorescent light by the calculation. Further, arithmetic unit 150 can calculate a fluorescent light image by using the relative spectral distribution of the fluorescent light. Moreover, arithmetic unit 150 can calculate a reflected light image by using each spectral information of light source 121 and light source 122, that is, the information about the relative spectral distribution of each excitation light.

Therefore, imaging device 100 can separate the fluorescent light image and the reflected light image from each of the captured images by using the plurality of images captured by the plurality of light sources.

Second Exemplary Embodiment

[2-1. Operation]

[2-1-1. Operation of Imaging Device]

A second exemplary embodiment is described with reference to FIGS. 3 and 4.

A configuration of an imaging device according to the second exemplary embodiment is similar to the configuration of the imaging device according to the first exemplary embodiment, and only operation of arithmetic unit 150 is different. Therefore, only the operation of arithmetic unit 150 is described in the second exemplary embodiment.

Figure 3:
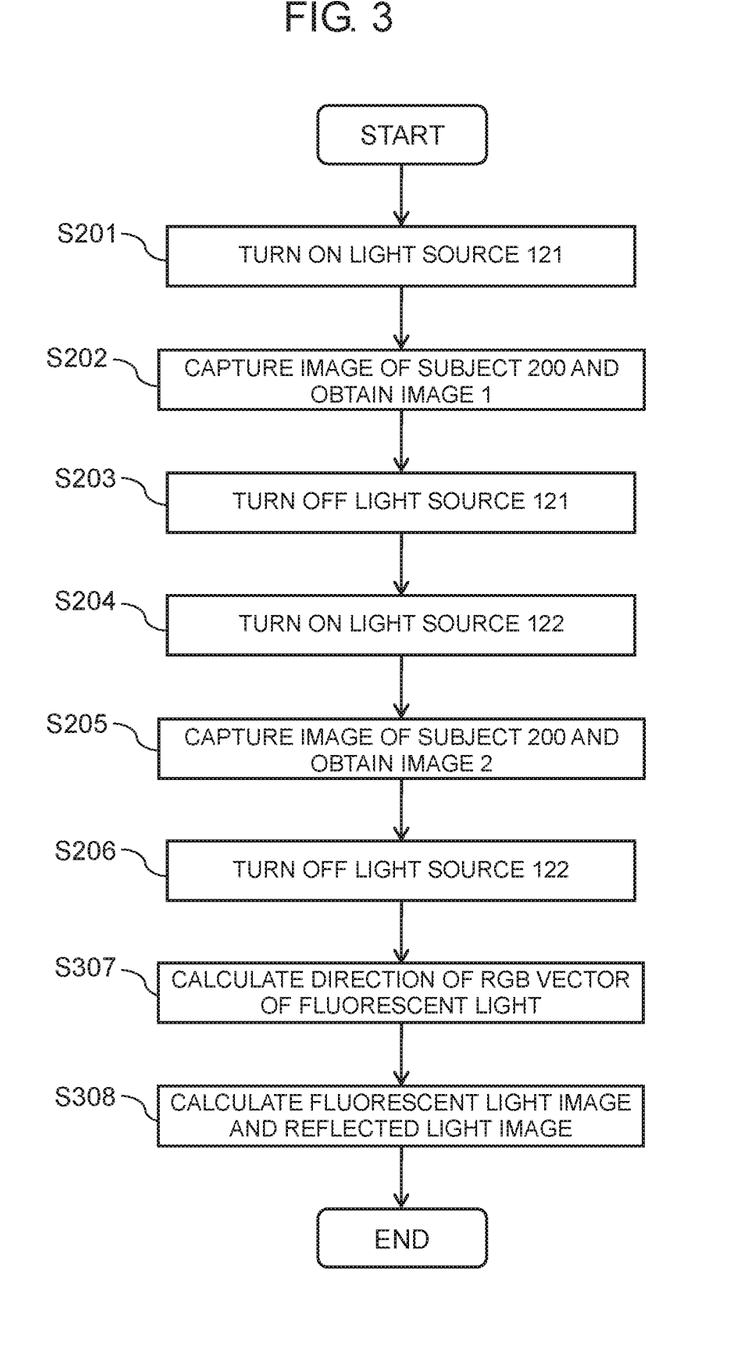
FIG. 3 is a flowchart for describing operation of an imaging device according to a second exemplary embodiment.

FIG. 3 is a flowchart for describing operation of imaging device 100. In FIG. 3, same reference marks are assigned to operation identical to the operation in the flowchart in FIG. 2, and description of the operation is omitted.

(Step S307) CPU 110 causes arithmetic unit 150 to calculate a direction of an RGB vector of fluorescent light in units of pixels by using image 1 and image 2 stored in memory 140 and RGB vectors of respective excitation light serving as respective spectral information of light source 121 and light source 122.

(Step S308) CPU 110 causes arithmetic unit 150 to respectively calculate a fluorescent light image and a reflected light image from image 1 and image 2 stored in memory 140. In other words, arithmetic unit 150 calculates the fluorescent light image and the reflected light image by using image 1 and image 2, the respective spectral information of light source 121 and light source 122, and the direction of RGB vector of the fluorescent light calculated in step S307.

[2-1-2. Calculation of Fluorescent Light Image]

In the first exemplary embodiment, arithmetic unit 150 solves equations in Formula 1, Formula 2 and calculates all the unknowns, thereby simultaneously calculating the fluorescent light image and the reflected light image. In the present exemplary embodiment, arithmetic unit 150 first calculates the direction of the RGB vector of the fluorescent light by the calculation in step S307.

The calculation is performed on pixels respectively located at spatially identical positions in image 1 and image 2. Similarly to the first exemplary embodiment, in a case where only one color value is included in one pixel, a color value that is not included in the pixel is created so that a plurality of color values are provided in one pixel by the interpolation process using color values of peripheral pixels.

Hereinafter, description is given using a pixel of captured subject 200 emitting the fluorescent light as a target. Further, the description is given using a pixel of captured subject 200 in image 1 as pixel p1 and a pixel spatially located at a same position as pixel p1 in image 2 as pixel p2.

Figure 4:
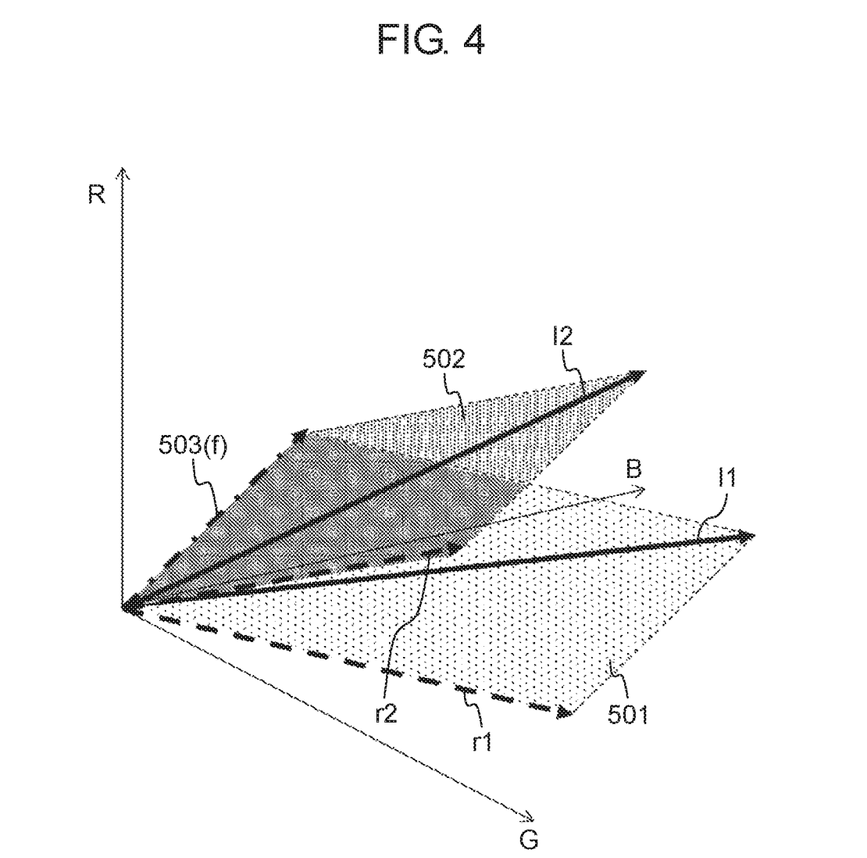
FIG. 4 is a view in which spectral distributions are represented by RGB vectors.

FIG. 4 is a view in which spectral distributions represented by three RGB values are represented by RGB vectors. As shown in FIG. 4, plane 501 includes vector I1 serving as an RGB vector of pixel p1 and vector r1 serving as an RGB vector of excitation light L1 stored in memory 140 in a three-dimensional RGB space. Similarly, plane 502 includes vector I2 serving as an RGB vector of pixel p2 and vector r2 serving as an RGB vector of excitation light L2 stored in memory 140 in the three-dimensional RGB space.

As described in the first exemplary embodiment, vectors indicating directions of RGB vectors of respective fluorescent light can be respectively represented as vector f in pixel p1, pixel p2. Accordingly, a direction of intersection line 503 between plane 501 and plane 502 is identical to a direction of vector f included in pixel p1 and pixel p2. Arithmetic unit 150 can calculate the direction of vector f by using this property.

The direction of intersection line 503 between plane 501 and plane 502 in the three-dimensional RGB space is calculated from an exterior product of perpendicular vectors of the two planes. Moreover, a direction of each of the perpendicular vectors of the planes can be calculated from an exterior product of two vectors that are included in the plane and are not parallel to each other. Accordingly, as in (Formula 3), the direction of vector f can be calculated from an exterior product of a vector obtained by an exterior product of vector I1 and vector r1 stored in memory 140 and an exterior product of a vector obtained by an exterior product of vector I2 and vector r2 stored in memory 140.

$$\vec{f} \propto (\vec{I1} \times \vec{r1}) \times (\vec{I2} \times \vec{r2}) \quad \text{(Formula 3)}$$

Here, a symbol of ∝ (proportion) is used to indicate that the direction of vector f is determined but a length (intensity) of vector f is not determined.

By performing the above-described calculation on all target pixels, arithmetic unit 150 can calculate an image including directional information of the RGB vectors of the fluorescent light from image 1 and image 2. In other words, arithmetic unit 150 can calculate the image reflecting relative spectral distribution of the fluorescent light. In the present exemplary embodiment, since the relative spectral distribution of the fluorescent light is represented by the RGB vectors, the image reflecting the relative spectral distribution of the fluorescent light is a color image. For example, it is possible that the length of vector f is normalized to 1 in all the pixels and that the image is calculated by using the normalized RGB vectors. This image can be utilized for a qualitative analysis.

[2-1-3. Separation of Fluorescent Light Image and Reflected Light Image]

The calculation in step S308 is described in detail. Similarly to step S307, the calculation is performed in units of pixels using the pixel of captured subject 200 emitting the fluorescent light as a target. Description is given using a pixel of captured subject 200 in image 1 as pixel p1 and a pixel spatially located at a same position as pixel p1 in image 2 as pixel p2.

The direction of vector f included in pixel p1 and pixel p2 obtained in step S307 corresponds to vector fin (Formula 1) and (Formula 2). Accordingly, the vector obtained by normalizing the length of vector f included in pixel p1 and pixel p2 to 1 can be applied to the second terms of (Formula 1) and (Formula 2). Since there are two unknowns ($a_1$, $b_1$) for three equations in (Formula 1) due to the application of vector f, $a_1$ and $b_1$ can be calculated. Likewise, since there are two unknowns ($a_2$, $b_2$) for three equations in (Formula 2), $a_2$ and $b_2$ can be calculated.

By performing the above-described calculation on all target pixels, arithmetic unit 150 can calculate the reflected light image and the fluorescent light image from each of image 1 and image 2. In other words, the reflected light image and the fluorescent light image included in image 1 are separated from image 1, and the reflected light image and the fluorescent light image included in image 2 are separated from image 2. Similarly to the first exemplary embodiment, since the reflected light image and the fluorescent light image respectively have the RGB vectors in the respective pixels, the reflected light image and the fluorescent light image are color images.

[2-2. Conclusion]

In imaging device 100 of the second exemplary embodiment, arithmetic unit 150 calculates the relative spectral distribution of the fluorescent light in the units of pixels by using image 1 and image 2 stored in memory 140 and the RGB vectors of the respective excitation light serving as respective spectral information of light source 121 and light source 122.

With this configuration, arithmetic unit 150 can first calculate the image of the directional information of the RGB vectors of the fluorescent light, that is, the image reflecting the relative spectral distribution of the fluorescent light.

Therefore, in a case where information about the intensity of the fluorescent light and the reflected light is not required and only qualitative information of the fluorescent light is required according to the use, imaging device 100 does not execute the calculation in step S308, thereby shortening calculation time.

Other Exemplary Embodiments

As described above, the first and second exemplary embodiments are described as an illustration of the technique disclosed in the present application. However, the technique of the present disclosure is not limited thereto, and can be also applied to exemplary embodiments in which changes, replacements, additions, omissions, and the like are made. Further, it is possible to form a new exemplary embodiment by combining the respective components described in the first and second exemplary embodiments.

Hence, other exemplary embodiments are illustrated below.

In the first exemplary embodiment, $b_1$ is set to 1. However, the present disclosure is not limited thereto, and $b_1$ may be set to any value provided that $b_1$ is a constant.

In the second exemplary embodiment, arithmetic unit 150 calculates the directional information of the RGB vector of the fluorescent light from the calculation of the exterior products. However, the present disclosure is not limited thereto. The directional information may be calculated by a method for solving an equation, that is, by using an equation representing the plane and the perpendicular relative to the plane in the space.

In the first and second exemplary embodiments, a number of light sources is two, and a number of colors that can be captured by imaging unit 130 is three (RGBs). However, the present disclosure is not limited thereto. Any configuration is employed provided that a number of equations exceed a number of unknowns. When the number of light sources is increased by one, the number of equations is increased by the number of colors that can be captured by imaging unit 130, and the number of unknowns is increased by two weights of reflected light and fluorescent light. When the number of colors that can be captured by imaging unit 130 by one from the three RGB colors, the number of equations is increased by the number of light sources, and the number of unknowns is increased by one element of the vector of the fluorescent light. For example, in a case where the number of light sources is three and the number of colors that can be captured by imaging unit 130 is four, the number of equations becomes 13 and the number of unknowns is 10. However, in a case where the number of equations is greater than the number of unknowns, an optimal solution of the unknowns can be obtained by using a technique, such as a least squares method. Further, in a case where the number of light sources and the number of colors that can be captured by imaging unit 130 are increased, it is also necessary to increase spectral information of the respective light sources stored in memory 140. Further, in a case where the number of light sources is increased, it is necessary to increase the number of captured images accordingly. Imaging unit 130 captures the images by the number of light sources.

In the first and second exemplary embodiments, the light source is the LED. However, the light source is not limited to the LED. The light source may be a light source that emits excitation light having spectral distribution of a narrow wavelength band. The light source may be, for example, a laser. Further, the light source may be a light source provided with a monochromator or an optical filter that transmits light having a specific wavelength. In a broad sense, any light source may be used as long as it can be considered that an RGB vector of reflected light including a spectral reflectance distribution of subject 200 and an RGB vector of excitation light are identical.

In the first and second exemplary embodiments, center wavelengths of the plurality of excitation light are 430 nm, 450 nm, respectively. However, the present disclosure is not limited thereto. Any wavelength can be used as long as subject 200 can generate fluorescent light. In other words, each of the plurality of light sources may be any light source provided that the light source emits the excitation light to cause subject 200 to emit the fluorescent light.

In the first and second exemplary embodiments, description is given using the pixel including the fluorescent light as an example. However, a pixel that does not include fluorescent light may also exist in a captured image. When a target pixel of calculation does not include the fluorescent light, arithmetic unit 150 cannot solve an equation for the pixel. Accordingly, arithmetic unit 150 may previously perform calculation to detect the pixel (a region) that does not include the fluorescent light in the captured image for each light source. In the method for detecting the pixel that does not include the fluorescent light, for example, there is a method for comparing a direction of an RGB vector of a pixel and a direction of an RGB vector of excitation light stored in memory 140. If the two directions are identical, it can be considered that a target pixel does not include the RGB vector and that the target pixel does not include fluorescent light. In the calculation of the direction of the RGB vector of the fluorescent light by the exterior product in the second exemplary embodiment, the exterior product for the pixel that does not include the fluorescent light becomes 0, if noise is not considered. Accordingly, arithmetic unit 150 may perform this calculation as the calculation to detect the pixel that does not include the fluorescent light. Arithmetic unit 150 calculates a relative spectral distribution of the fluorescent light using, as a target, a pixel that is not the detected pixel (region) that does not include the fluorescent light, that is, a pixel that includes the fluorescent light. Further, for example, using the pixel that does not include the fluorescent light as a target, arithmetic unit 150 may not perform the calculation in step S207, step S307, step S308, may set intensity of the fluorescent light to 0, or may define this information about the pixel in the captured image as information about reflected light.

In the first and second exemplary embodiments, an image of subject 200 is captured in the darkroom. However, the image of subject 200 may be captured in presence of ambient light. In this case, for example, arithmetic unit 150 calculates a difference image between a captured image captured by irradiating with excitation light and a captured image captured without irradiating with the excitation light. Since the difference image only includes reflected light and fluorescent light relating to the excitation light, it can be considered that the difference image is substantially equal to the captured image captured in the darkroom.

In the first and second exemplary embodiments, the length of the RGB vector of the excitation light stored in memory 140 is normalized to 1. However, the present disclosure is not limited thereto. The RGB vector of the excitation light may have any length. Whatever length the RGB vector has, only a value of weight corresponding to the length is changed accordingly. When a reflected light image is calculated, a vector that is a product of the weight and the RGB vector of the excitation light becomes constant. Further, the same applies to a length of the RGB vector of fluorescent light. The RGB vector of the fluorescent light may have any length. When a fluorescent light image is calculated, a vector that is a product of the weight and the RGB vector of the fluorescent light becomes constant.

In the first and second exemplary embodiments, the RGB value is used as the color information. However, the present disclosure is not limited thereto. For example, other color information, such as Y (yellow) or NIR (near infrared), may be used.

In the first and second exemplary embodiments, arithmetic unit 150 performs the calculation in step S207, step S307, step S308 on all the pixels. However, the present disclosure is not limited thereto. For example, arithmetic unit 150 may perform the calculation on only a part of the pixels of the captured image.

In the first and second exemplary embodiments, arithmetic unit 150 calculates the fluorescent light image and the reflected light image from the product of the weight and the RGB vector. However, the present disclosure is not limited thereto. An intensity image may be calculated from each of the weights ($a_1$, $b_1$, $a_2$, $b_2$) reflecting intensity information of the fluorescent light and the reflected light.

In the first and second exemplary embodiments, each spectral information of light source 121 and light source 122 stored in memory 140 is the RGB vector of each excitation light. However, the present disclosure is not limited thereto. Each spectral information may include a spectral distribution of each excitation light and a spectral sensitivity characteristic of the imaging element at finer intervals of a wavelength. In this case, arithmetic unit 150 calculates the RGB vector by integrating each spectral information in a wavelength direction. Further, memory 140 may store the spectral distribution of each excitation light and the spectral sensitivity characteristic of the imaging element separately, and arithmetic unit 150 may calculate the RGB vector of each excitation light by the calculation.

In the first and second exemplary embodiments, subject 200 emits the fluorescent light having the same relative spectral distribution by the irradiation with the plurality of pieces of excitation light. Even if subject 200 emits fluorescent light having different relative spectral distributions, it does not mean that the calculation cannot be performed at all. In that case, the relative spectral distribution is calculated while an error is included in information about a direction of the fluorescent light and information about intensity of the reflected light and the fluorescent light that are calculated. As long as the error is in a permissible range, the present disclosure can be also applied to subject 200 emitting the fluorescent light that does not have the same relative spectral distribution by the irradiation with the plurality of pieces of excitation light.

Arithmetic unit 150 may perform calculation that normalizes intensity of a fluorescent light image calculated from image 1 or image 2 by intensity of a reflected light image. For example, in a case where there is spatial intensity unevenness caused by the light source, or unevenness caused by shading of imaging unit 130, unevenness is also caused to an intensity distribution of the fluorescent light in the captured image due to an influence of the intensity unevenness or the like. In a region of subject 200 having identical reflectance, intensity distribution of the reflected light includes information about the intensity unevenness caused by the light source or the unevenness caused by the shading of imaging unit 130. Accordingly, the unevenness caused to the fluorescent light image due to the influence can be reduced by normalizing the intensity of the fluorescent light image by the intensity of the reflected light image.

In the first and second exemplary embodiments, memory 140 stores the information about the relative spectral distribution of the excitation light for each light source, and uses the information for the above-described calculation. However, memory 140 may store information about the relative spectral distribution of the reflected light for each light source obtained when subject 200 is irradiated with each excitation light, and may use the information for the above-described calculation. Specifically, it is possible that memory 140 stores the information about the respective relative spectral distributions of reflected light R1 and reflected light R2, and arithmetic unit 150 performs calculation by replacing vector r1 and vector r2 with the information about the relative spectral distributions of reflected light R1 and reflected light R2, respectively, in the above-described calculation. Arithmetic unit 150 can calculate a relative spectral distribution of fluorescent light, a fluorescent light image, and a reflected light image by using image 1 and image 2, and respective spectral information of reflected light R1 and reflected light R2, that is, RGB vectors of the respective reflected light.

In this way, if the relative spectral distribution of the reflected light for each light source is known in advance, each light source may be a light source having a wide wavelength band. However, when subject 200 is changed, a spectral reflectance distribution of subject 200, that is, the relative spectral distribution of the reflected light is changed. Accordingly, memory 140 is required to store the RGB vector of the reflected light for each light source according to subject 200. Further, arithmetic unit 150 is required to change the RGB vector of the reflected light used for the calculation according to subject 200.

In the first and second exemplary embodiments, arithmetic unit 150 calculates the fluorescent light image and the reflected light image from each of image 1 and image 2. However, the present disclosure is not limited thereto. Arithmetic unit 150 may calculate any fluorescent light image and reflected light image. It is necessary to use both image 1 and image 2 in the calculation when solving the equations in the first exemplary embodiment and in the calculation when calculating the direction of RGB vector of the fluorescent light in the second exemplary embodiment. However, arithmetic unit 150 can arbitrarily select which fluorescent light image and reflected light image to calculate after using images 1 and 2.

It should be noted that, since the aforementioned exemplary embodiments illustrate a technique of the present disclosure, various changes, replacements, additions, omissions, and the like can be made in the claims and their equivalents.

The present disclosure is applicable to a device that captures an image of fluorescent light emitted from a fluorescent substance (a subject) to analyze the substance. Specifically, the present disclosure is applicable to an endoscopic device, a fluorescent light observation device, an analysis device, an imaging device, and the like.

What is claimed is:

1. An imaging device comprising:
   a lighting unit having a plurality of light sources configured to emit excitation light having relative spectral distributions different from each other, the lighting unit causing each of the plurality of light sources to irradiate a subject with excitation light;
   an imaging unit configured to, for each of the plurality of light sources, simultaneously capture an image of fluorescent light emitted from the subject by the excitation light and an image of reflected light obtained by reflecting the excitation light by the subject, to generate a captured image;
   a memory configured to store information about a relative spectral distribution of the reflected light for each of the plurality of light sources; and
   an arithmetic unit configured to calculate a relative spectral distribution of the fluorescent light emitted from the subject by using the information about the relative spectral distribution of the reflected light for each of the plurality of light sources stored in the memory and the captured image for each of the plurality of light sources generated by the imaging unit.

2. The imaging device according to claim 1, wherein the information about the relative spectral distribution of the reflected light for each of the plurality of light sources is information about a relative spectral distribution of the excitation light for each of the plurality of light sources.

3. The imaging device according to claim 1, wherein the arithmetic unit detects a region that does not include fluorescent light in the captured image for each of the plurality of light sources, and calculates the relative spectral distribution of the fluorescent light by using a pixel that is not included in the detected region.

4. The imaging device according to claim 1, wherein the arithmetic unit calculates a fluorescent light image by using information about the relative spectral distribution of the fluorescent light and the relative spectral distribution of the reflected light.

5. The imaging device according to claim 1, wherein the arithmetic unit calculates a reflected light image by using information about the relative spectral distribution of the fluorescent light and the relative spectral distribution of the reflected light.

6. The imaging device according to claim 1, wherein the arithmetic unit calculates a fluorescent light image and a reflected light image by using information about the relative spectral distribution of the fluorescent light and the relative spectral distribution of the reflected light, and performs calculation to normalize intensity of the fluorescent light image by using intensity of the reflected light image.

7. The imaging device according to claim 1, wherein each of the plurality of light sources is a light source that emits the excitation light so as to cause the subject to emit the fluorescent light.

8. The imaging device according to claim 1, wherein each of the plurality of light sources is a laser.

9. The imaging device according to claim 1, wherein each of the plurality of light sources includes a monochromator.

10. The imaging device according to claim 1, wherein each of the plurality of light sources is an LED.

11. The imaging device according to claim 1, wherein each of the plurality of light sources includes an optical filter that transmits light having a specific wavelength.

12. The imaging device according to claim 1, wherein the imaging unit is an RGB camera.

13. An image processing method comprising:
irradiating a subject with excitation light from each of a plurality of light sources that emits excitation light having relative spectral distributions different from each other;
for each of the plurality of light sources, simultaneously capturing an image of fluorescent light emitted from the subject by the excitation light and an image of reflected light obtained by reflecting the excitation light by the subject, to generate a captured image; and
calculating a relative spectral distribution of the fluorescent light emitted from the subject by using information about a relative spectral distribution of the reflected light for each of the plurality of light sources and the captured image for each of the plurality of light sources.

* * * * *